US009999587B2

(12) United States Patent
Zheng et al.

(10) Patent No.: US 9,999,587 B2
(45) Date of Patent: Jun. 19, 2018

(54) COMPOSITIONS AND METHODS FOR STIMULATION MAGP-1 TO IMPROVE THE APPEARANCE OF SKIN

(71) Applicant: Avon Products, Inc., Suffern, NY (US)

(72) Inventors: Qian Zheng, Morris Plains, NJ (US); Siming W. Chen, Basking Ridge, NJ (US); Uma Santhanam, Tenafly, NJ (US); John W. Lyga, Basking Ridge, NJ (US)

(73) Assignee: Avon Products, Inc., Rye, NY (US)

( * ) Notice: Subject to any disclaimer, the term of this patent is extended or adjusted under 35 U.S.C. 154(b) by 147 days.

(21) Appl. No.: 14/848,443

(22) Filed: Sep. 9, 2015

(65) Prior Publication Data

US 2016/0008266 A1    Jan. 14, 2016

Related U.S. Application Data

(63) Continuation of application No. 13/158,947, filed on Jun. 13, 2011, now Pat. No. 9,132,294.

(60) Provisional application No. 61/360,083, filed on Jun. 30, 2010.

(51) Int. Cl.
| | |
|---|---|
| *A61K 36/00* | (2006.01) |
| *A61K 8/97* | (2017.01) |
| *A61K 8/46* | (2006.01) |
| *A61K 8/49* | (2006.01) |
| *A61Q 19/08* | (2006.01) |
| *A61K 31/5377* | (2006.01) |
| *A61K 36/185* | (2006.01) |
| *A61K 36/39* | (2006.01) |
| *A61K 36/53* | (2006.01) |
| *A61K 36/74* | (2006.01) |
| *A61K 45/06* | (2006.01) |
| *A61Q 19/00* | (2006.01) |

(52) U.S. Cl.
CPC .............. *A61K 8/97* (2013.01); *A61K 8/466* (2013.01); *A61K 8/49* (2013.01); *A61K 31/5377* (2013.01); *A61K 36/185* (2013.01); *A61K 36/39* (2013.01); *A61K 36/53* (2013.01); *A61K 36/74* (2013.01); *A61K 45/06* (2013.01); *A61Q 19/00* (2013.01); *A61Q 19/08* (2013.01); *A61K 2800/20* (2013.01)

(58) Field of Classification Search
CPC .................................................... A61K 36/00
See application file for complete search history.

(56) References Cited

U.S. PATENT DOCUMENTS

| | | |
|---|---|---|
| 4,322,438 A | 3/1982 | Peck |
| 6,146,640 A | 11/2000 | Dyke |
| 6,423,325 B1 | 7/2002 | Alaluf et al. |
| 7,514,092 B2 | 4/2009 | Dryer et al. |
| 7,618,662 B2 | 11/2009 | Hines et al. |
| 8,128,914 B2 | 3/2012 | Ptchelintsev et al. |
| 8,394,427 B2 | 3/2013 | Zheng et al. |
| 8,455,518 B2 | 6/2013 | Khusial et al. |
| 8,512,764 B2 | 8/2013 | Paufique |
| 8,771,758 B2 | 7/2014 | Ptchelintsev |
| 8,802,167 B2 | 8/2014 | Hwang et al. |
| 8,815,265 B2 | 8/2014 | Ptchelintsev et al. |
| 9,034,396 B2 | 5/2015 | Zheng et al. |
| 9,066,896 B2 | 6/2015 | Zheng et al. |
| 9,132,294 B2 | 9/2015 | Zheng et al. |
| 9,186,316 B2 | 11/2015 | Khusial et al. |
| 9,238,000 B2 | 1/2016 | Khusial et al. |
| 2003/0207818 A1 | 11/2003 | Jia et al. |
| 2003/0229083 A1 | 11/2003 | Debnath et al. |
| 2004/0126344 A1 | 7/2004 | Mahalingam et al. |
| 2004/0156886 A1 | 8/2004 | Kose |
| 2006/0013782 A1 | 1/2006 | Mahalingam et al. |
| 2006/0024390 A1 | 2/2006 | Schauss et al. |
| 2006/0134059 A1 | 6/2006 | Dryer et al. |
| 2006/0134231 A1 | 6/2006 | Hines et al. |
| 2006/0193819 A1 | 8/2006 | Lu et al. |
| 2007/0161625 A1 | 7/2007 | Brown et al. |
| 2007/0185038 A1 | 8/2007 | Bissett et al. |
| 2008/0193394 A1 | 8/2008 | Nam et al. |

(Continued)

FOREIGN PATENT DOCUMENTS

| | | |
|---|---|---|
| CN | 101559033 A  * | 10/2009 |
| CN | 101559033 A | 10/2009 |

(Continued)

OTHER PUBLICATIONS

Faraco et al. RecName: Full=Microfibrillar-associated protein 2; Short=MFAP-2; AltName: Full=Microfibrilassociated glycoprotein 1; Short=MAGP; Short=MAGP-1; Flags: Precursor. GenBank Accession No. P55001. Dec. 15, 2009; p. 1, definition.

Morton, J.; 1987. Bignay. p. 210-212. In: Fruits of warm climates. Julia F. Morton, Miami, FL.

Vasudesan, N,V.; Indian Medicinal Plants, vol. IV, Orient Longman Ltd, Chennai, 1995, 172.

Burkill, I.H.; (1966). "A Dictionary of the Economic Products of the Malay Peninsula. vol. II (I-Z)". Ministry of Agriculture and Cooperatives, Kuala Lumpur.

Kanchanapoom, T. et al.; "Iridoid glucosides from Thunbergia Iaurifolia". Phytochemistry 60:, 2002, p. 769-771.

Chopra. R. N.,et al.; C. Glossary of Indian Medicinal Plants (Including the Supplement). Council of Scientific and Industrial Research, New Delhi. 1986; Medicinal Plants of Nepal Dept. of Medicinal Plants. Nepal. 1993.

(Continued)

Primary Examiner — Qiuwen Mi
(74) Attorney, Agent, or Firm — Brian P. McCloskey; Elizabeth Morters

(57) ABSTRACT

The present disclosure relates to methods for treating, preventing and improving the condition and aesthetic appearance of skin, particularly, treating, preventing, ameliorating, reducing and/or eliminating fine lines and/or wrinkles of skin, by application of one or a combination of natural compounds or extracts that stimulate MAGP-1 expression and which improves the appearance of aged and/or photodamaged skin. The compositions of the invention are topically applied to the skin, or are delivered by directed means to a site in need thereof in an amount effective to improve the condition and aesthetic appearance of skin.

5 Claims, 2 Drawing Sheets

(56) References Cited

U.S. PATENT DOCUMENTS

| | | | |
|---|---|---|---|
| 2008/0274453 | A1 | 11/2008 | Hageman |
| 2009/0012155 | A1 | 1/2009 | Kim et al. |
| 2009/0012273 | A1 | 1/2009 | Nakamura et al. |
| 2009/0068126 | A1 | 3/2009 | Soares Romeiro et al. |
| 2009/0176810 | A1 | 7/2009 | Shin et al. |
| 2010/0158828 | A1 | 6/2010 | Ptchelintsev et al. |
| 2010/0166677 | A1 | 7/2010 | Ptchelintsev |
| 2010/0183528 | A1 | 7/2010 | Maloney et al. |
| 2010/0233128 | A1* | 9/2010 | Panasenko ............ A61K 8/922 424/93.4 |
| 2012/0003332 | A1 | 1/2012 | Zheng et al. |
| 2013/0053423 | A1 | 2/2013 | Lyga |
| 2013/0102606 | A1 | 4/2013 | Hwang et al. |
| 2013/0149268 | A1 | 6/2013 | Chen et al. |
| 2013/0149397 | A1 | 6/2013 | Chen et al. |
| 2014/0161910 | A1 | 6/2014 | Zheng et al. |
| 2014/0255523 | A1 | 9/2014 | Ptchelintsev et al. |

FOREIGN PATENT DOCUMENTS

| | | | |
|---|---|---|---|
| DE | 19910704 | A1 | 9/2000 |
| IN | 200201241 | I1 * | 11/2009 |
| JP | 2002087973 | A | 3/2002 |
| JP | 2003535026 | A | 11/2003 |
| JP | 2005511686 | A | 4/2005 |
| JP | 2005350435 | A | 12/2005 |
| JP | 2005350436 | A | 12/2005 |
| JP | 2006069954 | A | 3/2006 |
| JP | 2007026356 | A1 | 2/2007 |
| JP | 2007522259 | A | 8/2007 |
| JP | 2009506107 | A | 2/2009 |
| JP | 2009507826 | A | 2/2009 |
| JP | 2009508856 | A | 3/2009 |
| JP | 2010059196 | A | 3/2010 |
| JP | 2010090069 | A | 4/2010 |
| JP | 2014507132 | A | 3/2014 |
| WO | 2000053156 | | 9/2000 |
| WO | 2006068778 | A2 | 6/2006 |
| WO | 2007093839 | A1 | 8/2007 |
| WO | 2009018493 | A1 | 2/2009 |
| WO | 2010115491 | A2 | 10/2010 |
| WO | 2012005872 | A1 | 1/2012 |
| WO | 2012005876 | A2 | 1/2012 |

OTHER PUBLICATIONS

Pavanand et al.; Antimalarial Activity of Tiliacora triandra Diels against Plasmodium falciparum in vitro; Phytotherapy Research, vol. 3, No. 5, 1989, p. 215-217.

Weinbaum JS, et al.; Deficiency in Microfibril-associated Glycoprotein-1 Leads to Complex Phenotypes in Multiple Organ Systems; The Journal of Biological Chemistry, vol. 283, No. 37, Sep. 12, 2008, pp. 25533-25543.

Wagenseil JE, Mecham RP; New Insights into Elastic Fiber Assembly; Birth Defects Res C Embryo Today. Dec. 2007; 81(4):229-40.

Cleary EG, Gibson MA; Elastin-associated microfibrils and microfibrillar proteins; Int Rev Connect Tissue Res. 1983;10:97-209.

Gibson MA, et al. "The major antigen of elastin-associated microfibrils is a 31-kDa glycoprotein.". J. Biol. Chem. 261 (24), 1986, p. 11429-36.

Tiliacora Triandra Fresh 200 Leaves, 20 pages (2015).

Keratinocytes, 1 page (2015).

Revilla, Eugenio et al., "Comparison of Several Procedures Used for the Extraction of Anthocyanins from Red Grapes," J. Agric. Food Chem., vol. 46, pp. 4592-4597 (1998).

Choi, Eun-Mi et al., "Screening of Indonesian medicinal plants for inhibitor activity on nitric oxide production of RAW264.7 cells and antioxidant activity," Fitoterapia, vol. 76, pp. 194-203 (2005).

Fujimoto, Norihiro et al., "Expression of microfibril-associated glycoprotein-1 (MAGP-1) in human epidermal keratinocytes," Arch. Dermatol. Res. vol. 292, pp. 21-26 (2000).

Jothi, G. J. et al., "Glimpses of Tribal Botanical Knowledge of Tirunelveli Hills, Western Ghats, India," Ethnobotanical Leaflets, vol. 12, pp. 118-126 (2008).

Micor, Jose Rene L. et al., "Biological Activity of Bignay [*Antidesma bunius* (L.) Spreng] Crude Extract in Artemia salina," J. Med. Sci., vol. 5, No. 3, pp. 195-198 (2005).

Mintel, "Treatment Cream," Database GNPD [online], database accession No. 1646948 (2011).

Tatano, Yutaka et al., "Significant Decrease in Tropoelastin Gene Expression in fibroblasts from a Japanese Costello Syndrome Patient with Impaired Elastogenesis and Enhanced Proliferation," J. Biochem., vol. 140, pp. 193-200 (2000).

Durden et al., "Qualitative and Quantitative Mass Spectrometry of some Noncatecholic Biogenic Amines and Related Compounds as their Dansyl Derivatives," Biomedical Mass Spectrometry, pp. 83-95 (1974).

Hamburger Matthias et al., "Acetylated Saponins with Molluscicidal Activity from Sapindus rarak: Unambiguous Structure Determination by Proton Nuclear Magnetic Resonance and Quantitative Analysis," Phytochemical Analysis, vol. 3, pp. 231-237 (1992).

Thalib, A. et al., "The Effects of Saponin from Sapindus Rarak Fruit on Rumen Microbes and Performance of Sheep," (1996).

Kang, Sewon et al., "Topical N-Acetyl Cysteine and Genistein Prevent Ultraviolet-Light-Induced Signaling That Leads to Photoaging in Human Skin in vivo," The Society for Investigative Dermatology, Inc,; vol. 120, No. 5, pp. 835-841 (2003).

Nanasombat, S. et al., "Antimicrobial, antioxidant and anticancer activities of Thai local vegetables," Journal of Medicinal Plants Research, vol. 3, No. 5, pp. 443-449 (2009).

Singthong, Jittra et al., Extraction and physicochemical characterisation ofpolysaccharide gum from Yanang (*Tiliacora triandra*) leaves, Food Chemistry, vol. 114, pp. 1301-1307 (2009).

U.S. Appl. No. 13/710,617, filed Dec. 11, 2012, Zheng, Qian et al.
U.S. Appl. No. 12/648,581, filed Dec. 29, 2009, Lyga, John et al.
U.S. Appl. No. 13/305,779, filed Nov. 29, 2011, Zheng, Qian et al.
U.S. Appl. No. 14/284,869, filed May 22, 2014, Ptchelintsev, Dmitri.
U.S. Appl. No. 13/216,626, filed Aug. 24, 2011, Thorn Leeson, Daniel.
U.S. Appl. No. 13/710,536, filed Dec. 11, 2012, Hwang, Cheng et al.
U.S. Appl. No. 14/066,862, filed Oct. 30, 2013, Lyga, John W. et al.
U.S. Appl. No. 14/055,037, filed Oct. 16, 2013, Khusial, Permanan Raaj.
U.S. Appl. No. 13/158,947, filed Jun. 13, 2011, Zheng, Qian et al.
U.S. Appl. No. 14/669,545, filed Mar. 26, 2015, Lyga, John et al.
U.S. Appl. No. 14/661,061, filed Mar. 18, 2015, Khusial, Permanan Raaj.

* cited by examiner

COMPOSITIONS AND METHODS FOR STIMULATION MAGP-1 TO IMPROVE THE APPEARANCE OF SKIN

RELATED APPLICATIONS

This application claims priority to U.S. Provisional Patent Application Ser. No. 61/360,083, filed Jun. 30, 2010 and is a continuation of U.S. Nonprovisional patent application Ser. No. 13/158,947 filed on Jun. 13, 2011, the contents of both of which are hereby incorporated by reference in their entirety.

FIELD OF INVENTION

The present invention relates generally to methods of improving the aesthetic appearance of human skin and/or improving the appearance of aged and/or photodamaged skin by applying compounds to the skin which stimulate the expression of the extracellular matrix protein MAGP-1 and provide benefits to the skin.

BACKGROUND OF THE INVENTION

There is an increasing demand in the cosmetics industry to develop products that may be applied topically to the skin that improve the condition and appearance of skin. Consumers are interested in mitigating or delaying the dermatological signs of chronologically- or hormonally-aged skin, as well as skin aging due to the environmental stress, such as fine lines, wrinkles, sagging skin and other conditions due to a progressive loss of cell growth, proliferation and functionality in the epidermal and dermal skin layers. During the aging process, the complexion of the skin, i.e., the color and appearance of the skin, deteriorates slowly from aging and/or exposure to environmental stress, e.g., sunlight.

There remains a general need in the cosmetics industry for products that retard or counter the aging effects on the skin, and more specifically for products that produce such effects without undesirable side effects. In particular, there remains a need for topically applied cosmetic compositions that provide anti-aging and skin texture benefits using natural plant materials as active components.

Active ingredients or components derived or extracted from plants and plant seeds have commonly been employed for a myriad of medicinal, therapeutic and cosmetic purposes. Such actives may be obtained from the entire plant or various parts of a plant, such as seeds, needles, leaves, flowers, roots, bark, cones, stems, rhizomes, callus cells, protoplasts, and meristems. Active ingredients or components are incorporated in compositions in a variety of forms. Such forms include a pure or semi-pure component, a solid or liquid extract or derivative, or a solid natural plant material. Plant material may be incorporated in a variety of subforms such as whole, minced, ground or crushed, or otherwise physically modified for incorporation into a composition.

MAGP-1 (Microfibril-associated glycoprotein 1) is a small glycine rich acidic protein in extra-cellular matrix (ECM). MAGP-1 is a 30-33 kDa member of the microfibril associated glycoprotein family of proteins. It was found to be a key component of microfibrils and elastic fibers in skin. MAGP-1 forms complexes with other microfibril proteins such as fibrillin. Besides providing structural support for skin elastic fiber formation, MAGP-1 is also essential for vascular integrity, wound healing, and proper body fat deposition, possibly through regulating TGF-beta signaling, based on animal studies. MAGP-1 apparently mediates the release of Notch extracellular domain and also likely binds to type IV collagen and contributes to elastin fiber formation.

The present invention identifies a number of compounds and/or plant materials and extracts found to be active at simulating expression of the extracellular matrix protein MAGP-1. Among the plant materials, which preferably are in the form of extracts, are *Sesbania grandiflora, Antidesma bunius, Operculina turpethum, Ixora chinensis, Clerodendron lindleyi, Amorphophallus campanulatus, Tiliacora triandra*, and *Thunbergia laurifolia*. Suitable compounds are the tetrapeptide lysine-threonine-phenylalanine-lysine (Lys-Thr-Phe-Lys) (herein KTFK), thiodipropionic acid (TDPA) and its lower alkyl mono- and diesters, a substituted 2-(2-benzyl-1-benzimidazoyl) acetamide analog having the structure:

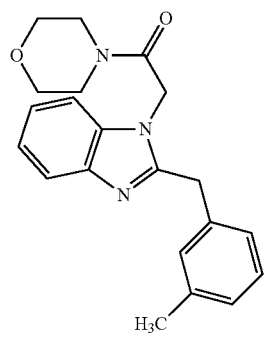 [SMILES: Cc1cccc(Cc2nc3ccccc3n2CC(=O)N2CCOCC2)c1]

and an N-substituted sulfonyloxybenzylamine having the structure:

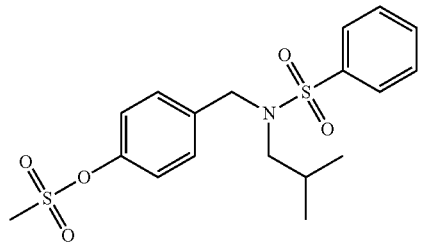

Certain of the MAGP-1 active plant species, namely, *Antidesma bunius, Operculina turpethum, Ixora chinensis*, and *Clerodendron linleyi*, including extracts of these plant species, have not been previously known for topical application to skin to improve the skin's aesthetic appearance. Similarly, the above-disclosed substituted 2-(2-benzyl-1-benzimidazoyl) acetamide analog and the N-substituted sulfonyloxybenzylamine as disclosed above have not been known previously for topical application to skin to improve the skin's aesthetic appearance.

*Antidesma bunius* is a species of fruit tree in the spurge family. It is native to Southeast Asia, the Philippines, and northern Australia. Its common Philippine name and other names include bignay, bugnay or bignai and currant tree. This is a variable plant which may be short and shrubby or tall and erect, approaching 30 meters in height. It has large oval shaped leathery evergreen up to about 20 centimeters long and seven wide. The leaves are sudorific and employed in treating snakebite, in Asia. (Morton, J. 1987. Bignay. p. 210-212. In: Fruits of warm climates. *Julia* F. Morton, Miami, Fla.).

*Operculina turpethum* is a plant in the morning glory family, (syn. *Ipomoea turpethum*) and is known commonly as turpeth, fue vao, and St. Thomas lidpod. It is one of many plants mentioned in the literature having claims of activity against liver disorders. Vasudesan, N, V., Indian Medicinal Plants, Vol. IV, Orient Longman Ltd, Chennai, 1995, 172. It also has anthelmintic expectorant, antipyretic, anti-inflammatory and purgative properties. Id.

*Ixora chinensis* is a fairly small, bushy shrub, usually only 5-10 ft tall. There are dwarf varieties that are much smaller. *Ixora* will flower when only a few inches high. It is commonly used a hedge or small garden plant. The plant is mainly grown as ornamental but its flowers are believed to have some medicinal uses including treatment for hypertension and for treating rheumatism, abscesses, bruises and wounds. The plant is native to India and Sri Lanka

*Clerodendron lindleyi* are shrubs, lianas, and small trees, usually growing to 1-12 m tall, with opposite or whorled leaves. The genus is native to tropical and warm temperate regions of the world, with most of the species occurring in tropical Africa and southern Asia, but with a few in the tropical Americas and northern Australasia, and a few extending north into the temperate zone in eastern Asia. Clerodendrum is from the Greek, meaning "lottery tree". *Dendros* meaning tree. The lottery refers to unsure possibility of medicinal value from certain plants of this genus.

*Sesbania grandiflora* (also known as agati, syn. *Aeschynomene grandiflora*) or hummingbird tree/scarlet wisteria is a small tree in the genus *Sesbania*. It is a fast-growing tree with a typical adult height of between 3 and 5 m. The leaves are regular and rounded and the flowers white and large, very characteristic. The fruits look like flat, long and thin green beans. The tree thrives under full exposure to sunshine and is extremely frost sensitive. It is believed to have originated either in India or Southeast Asia and grows primarily in hot and humid tropical areas of the world. Bark, leaves, gums, and flowers are considered medicinal. The astringent bark was used in treating smallpox and other eruptive fevers. (James A. Duke. 1983. Handbook of Energy Crops. unpublished.) *Sesbania grandiflora* was previously disclosed in U.S. Pat. No. 7,618,662, the disclosure of which is incorporated herein by reference.

*Thunbergia laurifolia* or Blue trumpet vine is an invasive species, which is used like an ornamental plant. This plant is found in Cerrado vegetation of Brazil. In Malaysia, juice from crushed leaves of *T. laurifolia* are taken for menorrhagia, placed into the ear for deafness, and applied for poulticing cuts and boils (Burkill, I. H. (1966). "A Dictionary of the Economic Products of the Malay Peninsula. Volume II (I-Z)". Ministry of Agriculture and Cooperatives, Kuala Lumpur). In Thailand, leaves are used as an antipyretic, as well as an antidote for detoxifying poisons (Kanchanapoom, T. et al. (2002). "Iridoid glucosides from *Thunbergia laurifolia*". Phytochemistry 60: 769-771).

KTFK is a synthetic tetrapeptide lysine-threonine-phenylalanine-lysine (Lys-Thr-Phe-Lys), known to be active in collagen and fibronectin synthesis. KTFK was previously disclosed in U.S. Patent Application Publication No. 2004/0126344, the disclosure of which is incorporated herein by reference.

*Amorphophallus campanulatus* is found in tropical regions from Madagascar to Asia, Polynesia and northern Australia. The root is carminative, restorative, stomachic and tonic. Chopra. R. N., Nayar. S. L. and Chopra. I. C. *Glossary of Indian Medicinal Plants* (Including the Supplement). Council of Scientific and Industrial Research, New Delhi. 1986; *Medicinal Plants of Nepal* Dept. of Medicinal Plants. Nepal. 1993. It is dried and used in the treatment of piles and dysentery. Id. The fresh root acts as an acrid stimulant and expectorant, it is much used in India in the treatment of acute rheumatism. Id. *Amorphallus campanulatus* was previously disclosed in U.S. Pat. No. 7,618,862, the disclosure of which is incorporated herein by reference.

Thiodopropionic acid (TDPA) is white crystalline solid having a slight characteristic odor and has demonstrated some antimicrobial and antioxidants activity. (WHO/Food Add./24.65 FAO Nutrition Meetings Report Series No. 38A). Thiodopropionic acid and its esters was previously disclosed in U.S. Patent Application Publication No. 2004/0126344, the disclosure of which is incorporated herein by reference.

*Sapindus rarak* is part of the *Sapindus* genus comprising about five to twelve species of shrubs and small trees in the Lychee family, Sapindaceae, native to warm temperate to tropical regions in both the Old World and New World. The extract of *Sapindus rarak* has demonstrated analgesic effects. *Sapindus rarak* was previously disclosed in U.S. Pat. No. 7,514,092, the disclosure of which is incorporated herein by reference.

*Tiliacora triandra* Diels of the *Tiliacora* family, also known as Yanang, is a species of flowering plant native to mainland Southeast Asia and used particularly in the cuisines of northeast Thailand and Laos. It is a climbing plant with mostly single, smooth, oval-shaped, deep green leaves and yellowish flowers. In traditional Southeast Asian medicine, *Tiliacora triandra* has been used as an herbal medicine for fever relief, alcohol intoxication, inflammation, and bacterial/fungal infection. For instance, the use of *Tiliacora triandra* Diels against *plasmodium falciparum* (cause malaria in humans) is disclosed in Pavanand et al., *Phytother. Res.*, 3, 215-217 (1989). *Tiliacora triandra* is the subject of a separate application filed concurrently with the instant application.

Safe, effective and new components of compositions to treat, prevent, reduce, inhibit and/or improve the dermatological signs of aging, including environmental stress, due to a progressive degradation of the epidermal and dermal skin layers, would be advantageous for the formulation of treatments and products for the skin. As described herein, novel and beneficial methods and compositions, as well as their mode of action, for the treatment of wrinkles and the like, as well as for personal care products for the skin, are provided herein.

SUMMARY OF THE INVENTION

It is an object of the present disclosure to provide a topical composition having a compound, particularly a natural plant material, blends thereof, or components therefrom, in an amount sufficient to improve the aesthetic appearance of human skin, and to prevent, ameliorate and/or reduce dermatological signs of chronologically or hormonally-aged or photo-aged skin, such as fine lines, wrinkles, sagging skin, and other conditions due to a progressive degradation of the skin cell growth, proliferation and functionality in the epidermal and dermal layer, where the plant material, blends thereof or components therefrom are in a cosmetically, dermatologically acceptable vehicle, carrier, or diluent.

It is another object of the present invention to provide compositions suitable for topical application to human skin having one or more MAGP-1 active agents that stimulate the expression of MAGP-1 comprising: (i) a plant material, especially extracts thereof, selected from *Antidesma bunius, Operculina turpethum, Ixora chinensis*, and *Clerodendron lindleyi*, and mixtures thereof, and (ii) a compound selected from 2-(2-benzyl-1-benzimidazoyl) acetamide analogs and an N-substituted sulfonyloxybenzylamine, and combinations/mixtures thereof.

It is another object of the present invention to provide a method of topically applying to human skin a composition having a compound, particularly a natural plant material, blends thereof, or components therefrom and which stimulate the expression of MAGP-1.

It is further object of the present disclosure to provide topical compositions comprising two or more ingredients wherein at least one first ingredient is selected from the group consisting of *Antidesma bunius, Operculina turpethum Ixora chinensis, Clerodendron lindleyi*, and an N-substituted sulfonyloxybenzylamine, and at least one second ingredient is selected from the group consisting of *Sesbania grandiflora, Amorphophallus campanulatus, Sapindus rarak, Tiliacora triandra, Thunbergia laurifolia*, tetrapeptide lysine-threonine-phenylalanine-lysine (KTFK), and Thiodipropionic acid (TDPA) and its esters, in an amount effective to treat, prevent, control, ameliorate, inhibit, and/or reduce dermatological signs of chronologically or hormonally-aged or photo-aged skin, such as fine lines, wrinkles, sagging skin, and other conditions due to a progressive degradation of the skin cell growth, proliferation and functionality in the epidermal and dermal layer.

It is still a further object of the present disclosure to provide a method of improving the aesthetic appearance of skin, including treating the effects of aging in the skin, by topically applying the compositions of the disclosure to the skin.

It is an additional object of the present disclosure to provide a screening method for identifying compounds that stimulate the expression of the MAGP-1 protein and to provide compositions using the actives identified in such screening method.

Further objects, features and advantages of the present disclosure will be better appreciated upon a reading of the detailed description.

In accordance with the foregoing objectives and others, it has surprisingly been found that expression of MAGP-1 in skin improves the appearance of aged or photodamaged skin by increasing elasticity, tightening pores, improving blood vessel integrity and reducing undereye dark circle, and reducing overall lines, wrinkles, and sagging.

DETAILED DESCRIPTION

All terms used herein are intended to have their ordinary meaning unless otherwise provided.

The present disclosure provides novel active agents and novel methods of improving the aesthetic appearance of human skin by topically applying compositions newly found to be effective to treat signs of aging and results relating to the dermatological aging of skin, such as fine lines, wrinkles, sagging skin, and other conditions, due to aging, including chronological aging, hormonal aging and/or photo-aging, to improve the aesthetic appearance of skin. It is to be understood that chronological aging represents the structural, functional, and metabolic changes in the skin that parallel the aging and degenerative change in other body organs, whereas photo-aging is a separate process and largely involves damage to the collagen and elastin fibers in the skin due to an exposure to environment such as the sunlight. Improvements in the aesthetic appearance of the skin may be achieved by topical application of these compositions to the skin on a regular and consistent basis, such as daily basis.

Figure 1:
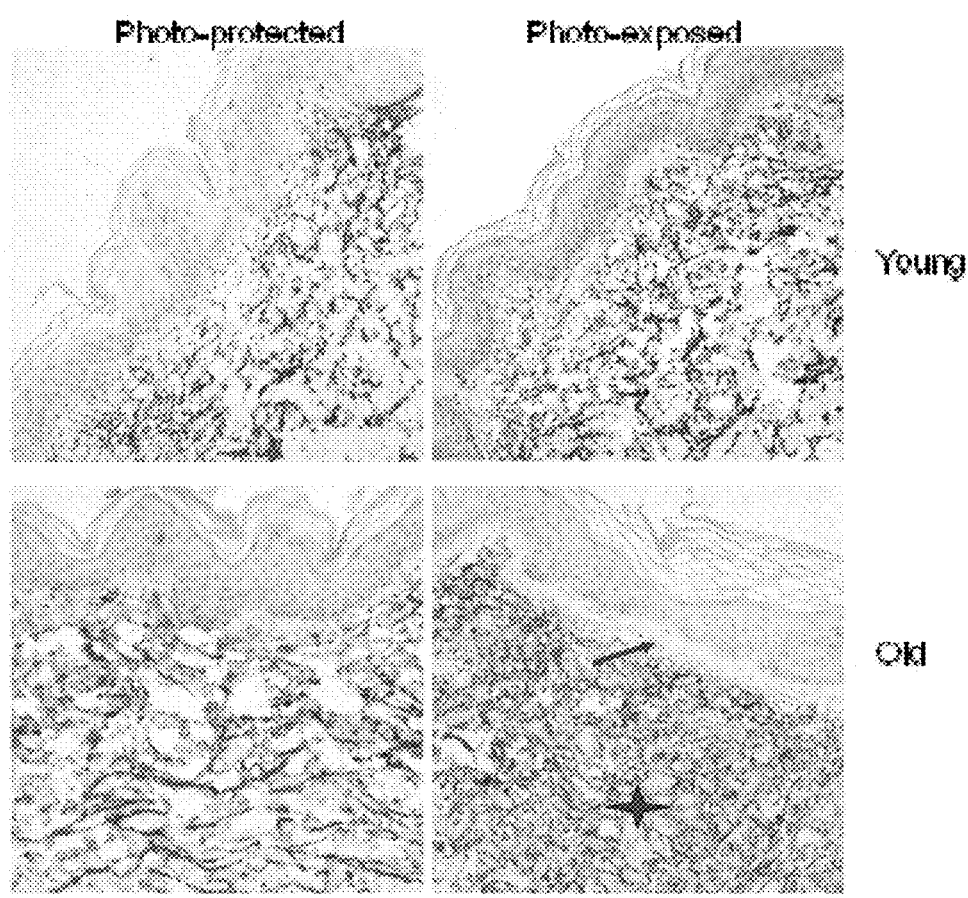
FIG. 1 illustrates the MAGP-1 protein expression in dermis of photo-protected and photo-exposed younger subjects (age 18-25) and older subjects (age 40-65).
Figure 2:
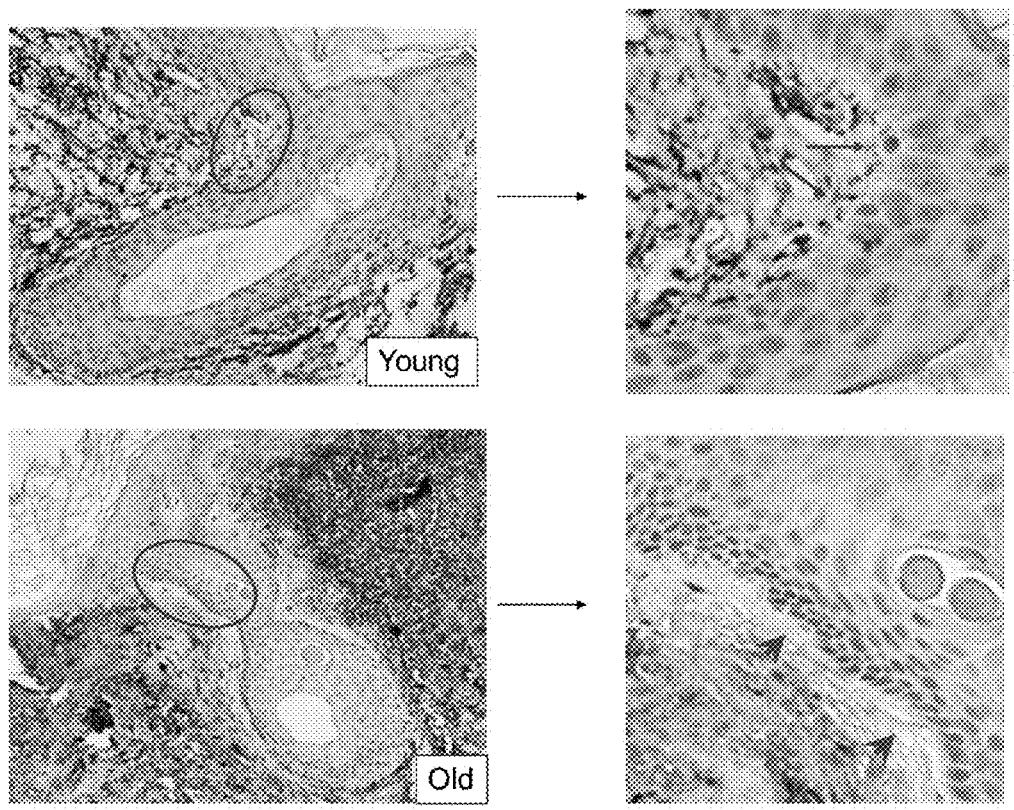
FIG. 2 illustrates the MAGP-1 expression around hair follicles and pores of the photo-protected and photo-exposed younger subjects (age 18-25) and older subjects (age 40-65).

It has been found, as demonstrated in FIGS. 1 and 2, and described in greater detail in the Examples, that MAGP-1 in skin tissue changes with age and photoexposure. Accordingly, aging skin will manifest a reduction in the number of MAGP-1 complexes formed with fibrillin and other microfibril proteins, with concomitant loss of skin elasticity, and numerous other properties of healthy skin. The compositions of the present invention containing one or more of the active agents for increasing MAGP-1 expression are provided to reduce, lessen, ameliorate the harmful effects of aging of skin, and to help restore a more youthful appearance to the skin.

Without wishing to be bound by theory, compounds and natural plant materials and extracts described herein (hereinafter, the MAGP-1 active agents) stimulate the expression of MAGP-1 in skin and improve the appearance of aged or photodamaged skin by increasing elasticity, tightening pores, improving blood vessel integrity, reducing undereye dark circles and reducing overall lines, wrinkles and skin sagging. It is believed that the expression of MAGP-1 forms complexes with microfibril proteins such as fibrillin. Fibrillin is a glycoprotein, which is essential for the formation of elastic fibers found in connective tissue. Fibrillin is secreted into the extracellular matrix by fibroblasts and becomes incorporated into the insoluble microfibrils, which appear to provide a scaffold for deposition of elastin the protein in connective tissue that is elastic and allows many tissues in the body to resume their shape after stretching or contracting.

The present disclosure provides novel compositions and their methods of use newly found to be effective to treat signs of aging and results relating to the dermatological aging including chronological aging, hormonal aging and/or photo-aging, of skin by effecting one or more of increasing elasticity, reducing fine lines, wrinkles, sagging skin, reducing undereye darkness/bruising and fat pockets, trimming/ slimming the effect of the fat pad improving skin tone, providing improved radiance and healthy glow, and other conditions.

Inasmuch as MAGP-1 stimulation increases formation of microfibril proteins such as fibrillin, which is secreted into the extracellular matrix by fibroblasts, it is a further embodiment of the invention to provide compositions that contain the MAGP-1 active agents of the present invention in combination with materials, plant or compounds, that have activity to increase proliferation of fibroblasts. Such combination increases production of collagen; provides an increase in anchoring and adhesion between keratinocytes, promotes cell-cell adhesion in the epidermis and dermis, and strengthens dermal-epidermal junctions. Collaterally, there is an improvement in the aesthetic appearance of the aging skin evidenced by an increase in one or more of skin firmness, skin plumpness, skin suppleness, or skin thickness.

The present invention further provides methods for topically applying a composition to the skin which improve the condition and appearance of skin by stimulating the expression of the extracellular protein MAGP-1.

The methods in accordance with the present invention incorporate one or a combination of MAGP-1 active agents comprising the compounds and/or plant extracts from the group consisting of *Sesbania grandiflora*, *Antidesma bunius*, *Operculina turpethum*, *Ixora chinensis*, *Clerodendron lindleyi*, tetrapeptide lysine-threonine-phenylalanine-lysine (KTFK), *Amorphophallus campanulatus*, thiodipropionic acid (TDPA) and its mono- and diesters of from 1 to 6 carbon atoms, *Sapindus rarak*, *Tiliacora triandra*, *Thunbergia laurifolia*, the N-substituted sulfonyloxybenzylamine having the structural formula I, namely, 4-((N-isobutylphenylsulfonamido)methyl)phenyl methanesulfonate (CAS 853758-16-4):

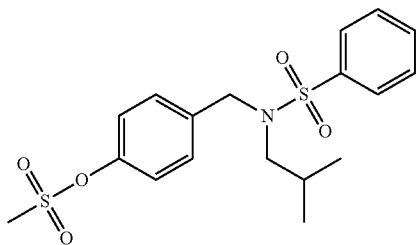 [SMILES: CC(C)CN(Cc1ccc(OS(C)(=O)=O)cc1)S(=O)(=O)c1ccccc1]

I and the substituted 2-(2-benzyl-1-benzimidazoyl) acetamide analog having the structural formula II, namely, 2-{2-[(3-methylphenyl)methyl]-1H-1,3-benzodiazol-1-yl}1-(morpholin-4-yl)ethan-1-one (CAS 1043743-29-8):

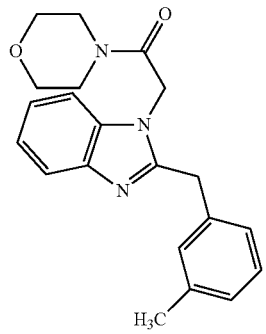

II

Compounds I and II are commercially available from AMRI Hungary, Zahony u 7, H-1031 Budapest, Hungary It is to be understood that, as used herein, the terms treating and treatment include and encompass reducing, ameliorating, improving, alleviating, and/or eliminating the dermatological effects of aging and/or environmental stress. The present compositions and methods are suitable for use in treating cosmetic and dermatological conditions of the skin in numerous areas of the body, including, without limitation, the face, forehead, lips, neck, arms, hands, legs, knees, feet, chest, back, groin, buttocks, and the like. In a preferred embodiment, the compositions are applied to the face.

One embodiment of the present disclosure relates to novel compositions comprising one or a combination of novel MAGP-1 active agents selected from the group of *Antidesma bunius*, the N-substituted sulfonyloxybenzylamine of structure I (above), the substituted 2-(2-benzyl-1-benzimidazoyl) acetamide analog of structure II (above), *Operculina turpethum*, *Ixora chinensis*, and *Clerodendron lindleyi*, and a cosmetically, dermatologically, or pharmacologically acceptable vehicle, and to methods for improving skin by topically applying to skin in need of treatment said novel topical compositions.

In another embodiment compositions of the present invention comprise one or more of the novel MAGP-1 active agents set forth above in combination with one or more other MAGP-1 active agents, and a cosmetically, dermatologically, or pharmacologically acceptable vehicle, and to methods for improving skin by topically applying to skin in need of treatment said novel topical compositions. Among the one or more other MAGP-1 active agents mention may be made of *Sesbania grandiflora*, KTFK, *Amorphophallus campanulatus*, thiodipropionic acid (TDPA) and its $C_1$ to $C_6$ alkyl mono- and diesters, *Tiliacora triandra*, and *Thunbergia laurifolia*.

Histological studies of the skin show that as aging occurs, the skin undergoes structural, functional, and metabolic changes that parallel the aging and degenerative changes in other body organs. While chronological and/or hormonal aging play a significant role, the number of wrinkles present is also highly dependent on the amount of exposure to environmental stress during an individual's life, e.g., repetitive sun exposure over 10, 20, 30, or more years of the person's life occasions oxidative damage from overexposure to ultraviolet (UV) sunlight. While there is a gradual thinning of male skin with increasing age of approximately 1% per year, the thickness of most women's skins remains surprisingly constant until the menopause, after which there is a significant and sometimes dramatic thinning with increasing age, reinforcing the need in older women for a treatment that increases the collagen content of skin and hence improves the firmness, thickness and plumpness of skin.

Thus, the successful restoration of youthful skin from this perspective must address a variety of key issues including: vitality of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen replacement, and mechanical properties of the skin. Cosmetic ingredients that addresses these key issues, are useful in the topical composition of the present disclosure.

Topical Compositions

The natural plant material may be in any form including, but not limited to, the whole plant, a dried plant, a ground plant, or parts thereof, including but not limited to, seeds, needles, leaves, roots, bark, cones, stems, rhizomes, callus cells, protoplasts, flowers, and meristems, or components and/or constituents found in, or isolated from, the natural plant material, and/or portions of the plant, or any combinations thereof. In one embodiment, the natural plant material is in the form of an extract derived from a select portion of the natural plant material. Typically, the plant extract is obtained from the whole plant or form the leaves of the plant. It is to be understood that "natural plant material" also includes an ingredient, component, constituent, or extract derived from the natural plant material.

In the case of *Tiliacora triandra*, the plant extract is preferably obtained from the vines of the plant. In the case of *Ixora chinensis* and *Sesbania grandiflora*, the extract is preferably obtained from the flowers of the plant. In the case of *Antidesma bunius*, *Thunbergia laurifolia*, and *Clerodendron lindleyi* the extract is preferably obtained from leaves.

In the case of *Operculina turpethum* the extract is preferably obtained from the aerial portion of the plant, i.e., the whole plant excluding the roots.

Insofar as *Tiliacora triandra* compositions are concerned in connection with the present invention, the present invention contemplates embodiments excluding hydrogen peroxide, iodine, tarrow root and a mixture of tarrow root and iodine.

The composition comprising these plants is effective when topically applied, preferably in a daily manner.

The compositions have a concentration of the MAGP-1 active agents of from about 0.0001 wt % to about 90 wt %, about 0.001 wt % to about 25 wt %, about 0.01 wt % to about 10 wt % based on the total weight of the composition, about 0.05 wt % to about 1 wt %. In the case of plant extracts, the above amounts refer to an "active amount" of the plant extract. The terms "active amount" or "dry weight" are used synonymously and refer to the amount of the plant extract after solvent and/or other diluents have been removed. One of ordinary skill in the art would be able to adjust the amount of extract used based upon the specific application or effect desired.

The MAGP-1 active agents of the present disclosure are preferably contained in a cosmetically or dermatologically acceptable vehicle, medium, diluent or carrier. In an embodiment embracing topical application, the compositions of this disclosure comprise a medium (vehicle, diluent or carrier) that is compatible with human skin. The compositions can be formulated as aqueous, alcohol, or aqueous/alcohol-based solutions, ointments, lotions, gels, water-in-oil, oil-in-water, of water-oil-water triple emulsions having the appearance of a cream or gel, microemulsions, or aerosols. In addition, the compositions can be in the form of vesicular dispersions containing ionic and/or nonionic lipids, as described above. Dosage units suitable for such compositions are formulated according to the conventional knowledge and techniques used in the art.

Methods of Using MAGP-1 Active Agents

As will be appreciated by the practitioner, cosmetic treatments comprising compositions containing natural plant materials, including extracts, components, and/or constituents of the invention may be carried out, for example, by topically applying the cosmetic composition as described herein according to a regimen for administering such compositions. The topical cosmetic composition preferably is applied once or twice daily (e.g., morning and evening) for a period of at least one week, but may include a period of about 2, 4, 8, or 12 weeks. The consumer may wish to continue use of the composition for an extended period of time. The cosmetic composition is preferably applied to the face and neck, but may be applied to any area of skin in need of aesthetic improvement, where the cosmetic composition remains on the affected area of skin, and preferably not removed or rinsed off the skin. The methods encompass the application of compositions/products in the form of creams, lotions, gels, masks, sera, ointments, patches, makeup, makeup-removing milks, sunscreen compositions, or the like, to the skin. Preferably the cosmetic composition is a topical leave on formulation, where spraying as a form of application is also envisioned.

In a particular embodiment of the invention, the topical compositions having an MAGP-1 active agent of the present invention, including compositions containing two or more of such agents, and compositions containing one or more novel active agents as previously defined, alone or in combination with one or more other active agents, including components or extracts derived therefrom, are useful for improving the condition and aesthetic appearance of skin affected by aging, particularly matured or maturing skin, by anyone of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; ameliorating the effects of estrogen imbalance; preventing and/or treating skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

The active components of the disclosed topical composition are further useful in treating, preventing, arresting, ameliorating, reducing or diminishing medical and/or dermatological conditions of skin affected by aging. Such conditions, as used herein, commonly include, but are not limited to, dermatological aging (chronological aging, hormonal aging and/or actinic aging), dermatitis, skin and hair fragility, rosacea, skin blemishes, sensitive skin, hyperpigmentation or hypopigmentation, thinning skin, roughness, keratosis, skin atrophy, wrinkles, lines, hyperplasia, fibrosis, and any combinations thereof. The active components of the topical composition may also be useful in enhancing the general health, vitality, condition, and appearance of the skin.

Gene expression may be measured by the determination of RNA levels in cultured cells, for example, using techniques such as Northern blot technology and the polymerase chain reaction (PCR), e.g., "real time" PCR and reverse transcription PCR (RT PCR) as practiced in the art. (see, e.g., Sambrook et al., 1989, *Molecular Cloning: A Laboratory Manual*, Cold Spring Harbor Laboratory, Cold Spring Harbor, New York; R. Higuchi et al., 1992, *Biotechnology*, 10:413-417; R. Higuchi et al., 1993, *Biotechnology*, 11: 1026-1030; E. S. Kawasaki, 1990, "Amplification of RNA", In: *RNA Protocols: A Guide to Methods & Applications*, M. A. Innis et al., Academic Press, San Diego, Calif., pp. 21-27; all of which are herein incorporated by reference). In addition, gene expression in skin, skin substitute, or cultured cells may be evaluated using gene (cDNA) arrays (microarrays or nucleic acid gene chip test arrays comprising membrane, glass, plastic or silicon support materials or the like), serial analysis of gene expression (SAGE), (e.g., as described by V. E. Velculescu et al., *Science*, 270(5235): 484-487, 1995; A. Lal et al., *Cancer Res.*, 59(21):5403-5407, 1999; both of which are herein incorporated by reference), or differential display techniques all of which are commonly known and used in the art.

The topical compositions use plant materials/active ingredients affected by genes associated with dermatological signs of aging, such as fine lines, wrinkles, and sagging skin as a biomarker for compounds which may improve the condition and appearance of affected skin. If expression levels of such nucleic acid/protein biomarkers are modified or elevated in the presence of a natural plant material or active ingredient therefrom, the natural plant material may be used in a topical composition of the invention for improving the condition and appearance of skin. Such expression level assays embrace a variety of methods for measuring nucleic acid levels in cells that have been exposed to one or more test substances. Suitable methods include detection and evaluation of gene activation or expression of, for example, DNA, RNA, or mRNA. As non limiting examples, polymerase chain reaction (PCR) assays (e.g., R T-PCR), Northern blotting, in situ hybridization, and other assays as known and practiced in the art may be employed to quantify RNA in cells being assayed for tolerance to a particular treatment (see, e.g., J. O'Connell, 2002, RT-PCR Protocols, Humana Press, Totowa, N.J.; R. Rapley and D. L. Manning, 1998, *RNA Isolation and Characterization Protocols*, Humana Press; R. Rapley, 2000, *Nucleic Acid Protocols Handbook*, Humana Press; all of which are herein incorporated by reference). In accordance with such assays, if levels of at least one nucleic acid biomarker are elevated in the presence of one or more test substances, this may predict that the substance(s) will improve the dermatological signs of aging. These substances, or natural plant materials, may then be used in a topical composition, preferably applied daily to the skin, in order to treat, prevent, ameliorate, and/or reduce, signs of dermatological aging, especially fine lines, wrinkles, and sagging skin, thereby improving the condition and aesthetic appearance of skin.

In another embodiment, the plant extract as used herein, also includes "synthetic" extracts, i.e., various combinations of known plant components and/or constituents that are combined to substantially mimic the composition and/or activity of a plant extract of natural origin. Such synthetic extracts are included in the term "plant extract". The synthetic extracts will have two or more, three or more, or four or more active ingredients in common with a plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality". Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

For use in the compositions of this disclosure, the plant extract or components and/or active constituents are preferably derived directly from the plant. The components may be in a pure form, a semi-pure form, or unpurified form. In one embodiment, the components are in the form of an extract obtained by organic solvent extraction.

Methods of extraction using organic solvents are known in the art and may be used in accordance with the present invention. Briefly, one organic solvent extraction method involves washing and extracting the plant material using an organic solvent. Non-limiting examples of organic solvents include methanol, ethanol, isopropanol, dichloromethane, chloroform, hexane, xylene, and petroleum ether. Well-known methods in the art may be used for organic solvent extraction.

Organic solvent extraction involves collecting the raw materials from the plant that contain the desired constituent(s), such as seeds, needles, leaves, roots, bark, cones, stems, rhizomes, callus cells, flowers, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time adapted to remove the plant constituents is suitable, with between about 1-8 hours typical, more preferably is between about 2-6 hours, and most preferably is between about 3-5 hours. The temperature of extraction is between about 30° C. about 90° C., between about 40° C. about 70° C., and between about 50° C. about 60° C. The collected extract is then fine-filtered to remove debris, and may be used directly, or is concentrated, for example by distilling the solvent or by other conventional processing, and the extract can also be provided in powder form.

Similarly, aqueous-organic solvent extraction involves initially collecting raw materials from a plant containing the desired alkaloid(s), such as seeds, needles, leaves, roots, bark, cones, stems, rhizomes, flowers, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract actives from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Extracts may also be obtained by extracting the plant material with water, ethanol, or a mixture thereof. The hydroalcoholic solvent systems may comprise from about 10% by volume to about 90% by volume of ethanol and from about 10% by volume to about 90% by volume of water. More typically, the solvent system will comprise from about 40% by volume to about 90% by volume of ethanol and from about 10% by volume to about 60% by volume of water.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

The extracts can be used in admixture with physiologically acceptable solvents, as concentrates in which a portion of the solvent or other diluents are removed by evaporation or other suitable physical processes, or preferably the solvent can be removed to provide a dried extract. Preferably solids are removed from the extract by filtering, centrifuging, or other suitable processes. Drying may be conducted by lyphilization, spray drying, prilling, or other suitable process. Spray drying may be conducted by combining the extraction liquid with a filler such as maltodextrin, followed by spray drying.

Suitable extraction processes are disclosed in PCT Publications WO03/079816 (describes a process for the preparation of tomato extracts with high content in lycopene), WO04/014404 (describes a process for the preparation of an *Echinacea angustifolia* extract) and WO04/014958 (describes extracting a polysaccharide of *Echinacea angustifolia* roots), all of which are herein incorporated by reference in their entirety.

Vehicle and Compositions

In accordance with this disclosure, the compositions containing the MAGP-1 actives of the invention can further comprise anti-oxidants, anti-inflammatories, sunscreens, cosmetics, including make-ups, anti-aging formulations, e.g., creams for fine lines and/or wrinkles, topicals, skin penetration enhancers, sprays, and the like. Also in accordance with this disclosure, the plant components and additional ingredients comprising such compositions can be formulated in a variety of product forms. Preferably, the compositions are prepared in targeted delivery systems, e.g. creams, lotions, gels, serums, transdermal patches, and the like, particularly for topical administration. Targeted delivery and/or penetration enhancement may also be achieved by iontophoresis.

The present disclosure further provides the compositions comprising the plant components preferably for topical administration or for targeted delivery without inducing significant irritation. Thus, the inventive compositions are especially suitable for sensitive skin. The compositions are applied to the skin for a period of time sufficient to improve the aesthetic appearance of skin. The compositions are preferably applied topically once, twice, or more daily, preferably, once or twice daily. The daily application is preferably for a period of one week, two weeks, four weeks, or more. The compositions can be formulated into liposomes or other encapsulates or delivery vehicles which can comprise other additives or substances, and/or which can be modified to more specifically reach or remain at a site following administration.

The present disclosure also encompasses compositions comprising a cosmetically or dermatologically acceptable formulation which is suitable for contact with living animal tissue, including human tissue, with virtually no adverse physiological effect to the user. Compositions embraced by this disclosure can be provided in any cosmetically and/or dermatologically suitable form, preferably as a lotion or cream, but also in an anhydrous or aqueous base, as well as in a sprayable liquid form. Other suitable cosmetic product forms for the compositions of this disclosure include, for example, an emulsion, a lip balm, a lip gloss, a lotion, a mask, an ointment, a mousse, a patch, a pomade, a solution, a spray, a wax-based stick, or a towelette. In addition, the compositions contemplated by this disclosure can include one or more compatible cosmetically acceptable adjuvants commonly used and known by the skilled practitioner, such as colorants, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and the like, as well as other botanicals such as aloe, chamomile, and the like, and as further described below.

Cosmetically or dermatologically acceptable vehicles that can be used in the present topical compositions include, but are not limited to, one or more aqueous systems, glycerins, C1-4 alcohols, fatty alcohols, fatty ethers, fatty esters, polyols, glycols, vegetable oils, mineral oils, liposomes, laminar lipid materials, silicone oils, water or any combinations thereof.

In the present disclosure, the vehicle may be in the form of an aqueous phase, an oil phase, a gel, a wax-in-water emulsion, a silicone-in-water emulsion, a water-in-silicone, an oil-in-water emulsion, or a water-in-oil emulsion. The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, digylcerol, panthenol, or polyethylene glycol, and mixtures thereof. This aqueous phase may represent from about 0.5 to about 99.99 wt % by weight of the composition.

When the composition of the disclosure is in the form of an emulsion, it can also optionally comprise a surfactant, preferably in an amount of from 0.1 to 30% and in particular from about 1 to about 20 wt % by weight of the composition.

The composition can also comprise a thickening polymer such as an amphiphilic polyurethane, a polyacrylic homopolymer or copolymer, a polyester, and/or a hydrocarbon-based resin. The polymers can be dissolved or dispersed in the cosmetically acceptable vehicle and optionally combined with a plasticizer.

The composition of the disclosure may also comprise an oil phase containing oil soluble or oil dispersible ingredients that are liquid at room temperature (25° C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely, for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of 0 wt % to about 90 wt %, preferably from about 1 wt % to 80 wt % by weight of the oil phase.

The oil phase of the composition of the disclosure may also comprise one or more cosmetically acceptable organic solvents. These solvents are present in an amount of 0 wt % to about 60 wt %, preferably about 1 wt % to 30 wt % by weight of the composition and can be selected from the group consisting of lipophilic organic solvents, amphiphilic organic solvents and mixtures thereof. Suitable solvents which can be used in the composition of the disclosure include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the disclosure may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 wt % to about 20 wt % by weight of the composition. The nature of these ingredients and their amounts must be compatible with the production of the compositions of the disclosure.

The composition of the disclosure may also comprise an additional particulate phase, typically present in an amount of 0 wt % to about 30 wt % by weight of the composition, preferably from about 0.05 wt % to about 20 wt %, and which can comprise fillers, pigments and/or pearlescent agents and/or fillers used in cosmetic compositions. Suitable inorganic pigments include titanium oxide and iron oxide; suitable fillers include talc, mica, polyethylene powder boron nitride, copolymer microspheres, and silicone resin microbeads (Tospearl from Toshiba).

The oil phase of the compositions of the disclosure may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present disclosure may contain from 0 to about 20 wt % waxes by weight of the composition. The gums are generally high molecular weight PDMSs or cellulose gums or polysaccharides and the semisolid materials are generally hydrocarbon-based compounds such as lanolins and derivatives thereof or alternatively PDMSs. The compositions of the present disclosure may contain from 0 to about 20 wt % gums by weight of the composition, typically from about 0.1% wt to about 10 wt %.

In another preferred embodiment, the topical compositions of the present disclosure also include at least one of the following: a skin penetration enhancer, a surface smoother, a skin plumper, an optical diffuser, a sunscreen, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety.

Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

An antioxidant functions, among other things, to scavenge free radicals from skin to protect the skin from environmental aggressors. Examples of antioxidants that may be used in the present compositions include but are not limited to alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred antioxidant are 3,6,9-trioxaundecanedioic acid, glycolic acid, lactic acid, or any mixtures thereof; compounds having phenolic hydroxy functions, such as ascorbic acid and its derivatives/esters; beta-carotene; catechins; curcumin; tetrahydrocurcumin; tocopherol and its derivatives; or any mixtures thereof. Compositions of the present disclosure may have an antioxidant preferably from about 0.001 wt % to about 10 wt %, and more preferably from about 0.001 wt % to about 5 wt %, of the total weight of the composition.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to about 20% of the total weight of the composition.

Non-limiting examples of active agents for formulating into the compositions of the present disclosure include those reagents having an effect on the treatment of wrinkles and/or fine lines, in addition to the natural plant actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to about 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

More particularly, the compositions for topical application can be in the form of a protective care composition for the skin, preferably for the face, the neck, the hands, the feet, or other areas of the body. Non-limiting examples include day creams or lotions, night creams or lotions, sunscreen creams, lotions, or oils, body milks, makeup (a foundation), artificial tanning compositions, depilatories, and patches.

Emulsifiers are typically present in emulsion compositions of the disclosure in an amount of about 0.1% to about 30%, by weight and preferably from about 0.5% to about 30% by weight relative to the total weight In water-based formulations, the active compounds can be formulated in the pH range from 1 up 8, with pH=2-7 being preferred, and pH 3.5-5.5 being most preferred.

In another embodiment in accordance with the present invention, compounds for stimulating the expression of MAGP-1 protein are screened for activity using an assay or screening method which involves culturing normal human dermal fibroblasts in plates with DMEMD with 10% serum followed by incubation for 24 hours at 37° C. and 10% $CO_2$. After 24 hours stock solutions of compounds of the present invention as test materials were made in appropriate solvents (e.g., DMSO). The cells are then treated with the test materials or respective vehicle control diluted in growth medium for 48 hours in a humidified 37° C. incubator with 10% $CO_2$. After incubation, growth medium is typically removed and a TRIzol reagent is added to the plates. The resulting cell lysates are collected and placed in a freezer until RNA isolation and analysis. RNA isolation can be performed using any method known to those of skill in the art. After isolation, concentration of total RNA is determined by Nanodrop (Thermo Scientific, DE) or any other known method. The isolated RNA then undergoes Reverse Transcription (RT) and quantitative Polymerase Chain Reaction (qPCR) to amplify the RNA, followed by measurement and calculation according to known methods to determine the level of MAGP-1 stimulation activity of each compound.

A further embodiment of the invention is to prepare compositions containing a MAGP-1 active identified in accordance with the above-disclosed screening method.

The following examples are meant to demonstrate certain aspects of the invention in a non-limiting fashion.

EXAMPLES

Example 1

Preparation of Extracts

*Ixora chinensis*—An extract is obtained by extracting the dry chopped plant of *Ixora chinensis* Lamk. plant using an ethanol extraction followed by a further extraction with hexane. Briefly, the chopped plant of *Ixora chinensis* is first manually ground into small particles resulting in a powder of about 250 grams. The ground powder is then extracted with 50% ethanol. After filtering and vacuum evaporation, the total concentrated extract is diluted with water, centrifuged and filtered. The liquid is then thrice extracted with hexane, the hexane upper layer being discarded and the aqueous layer being lyophilized resulting in an extract of about 90 grams.

*Clerodendron linleyi*—An extract is obtained by extracting leaves of the *Clerodendron linleyi* plant using an ethanol extraction scheme. The leaves of *Clerodendron linleyi* are first manually ground into small particles resulting in a powder of about 250 grams per flask (2 flasks). The ground powder is then extracted with 80 vol % ethanol (2×2,000 ml per flask). After filtering and vacuum evaporation, the total concentrated extract is lyophilized resulting in an ethanolic extract of 30.77 grams.

*Antidesma bunius*—An extract is obtained from 400 grams of ground plant leaves extracted with 4450 ml of a 1:1 ethanol-water solution by volume in three portions. The extract is filtered, concentrated under vacuum to remove ethanol, diluted with water to 1300 ml, and then centrifuged. The resulting supernatant liquid is washed with 500 ml of dichloromethane, decolorized with 10 g of charcoal, filtered, then concentrated to yield 57.7 g of extract, which is dried to a powder.

*Operculina turphetum*—An extract is obtained by extracting the aerial portions of the *Operculina turphetum* plant using an ethanol extraction scheme. The leaves of *Operculina turphetum* are first manually ground into small particles resulting in a powder of about 250 grams. The ground powder is then extracted with a water-ethanol mixture (50-50). After filtering and vacuum evaporation, the aqueous solution is washed with methylene chloride, concentrated under vacuum and dried.

*Tiliacora triandra*—An extract is obtained by extracting the vine of the *Tiliacora triandra* plant using an ethanol extraction scheme. Briefly, the vines of *Tiliacora triandra* Diels are first manually ground into small particles resulting in a powder of about 250 grams per flask (2 flasks). The ground powder is then extracted with 80% ethanol (2×2,000 ml per flask). After filtering and vacuum evaporation, the total concentrated extract ias lyophilized resulting in an ethanolic extract of 50 grams.

Example 2

MAGP-1 Expression in Dermis

Materials and Methods

Skin biopsies were obtained from both photo-exposed and photo-protected areas of 15 younger subjects (age 18-25)

and 15 older subjects (age 40-65). Tissues were fixed in formalin and subject to immunohistochemistry study. Anti-MAGP-1 and Alkaline phosphatase-conjugated secondary antibody were applied accordingly to visualize protein localization in skin. Images were taken by Zeiss Axionskop2 microimaging system.

Results

MAGP-1 protein is structurally degraded with photoaging (FIG. 1). The arrow in FIG. 1 indicates the absence of MAGP-1 fibrils in papillary dermis. The star indicates structural degradation of MAGP-1 in dermis.

Example 3

MAGP-1 Expression Around Pores and Hair Follicles

Using similar materials and methods as set out in Example 2, the results here demonstrated that MAGP-1 protein level is significantly reduced around hair follicle/pores with photoaging (FIG. 2). The arrows in FIG. 2 indicate high levels of MAGP-1 fibril structure around hair follicle/pore from younger subjects; and arrowheads indicate the absence of MAGP-1 around hair follicle/pore in photoexposed skin from older subjects.

Example 4

Screening Method

Cell Treatment

Normal human dermal fibroblasts (Cascade Biologics) were cultured in 100 mm plates with 10 ml of DMEM with 10% serum and incubated for 24 hours at 37° C. and 10% $CO_2$. After 24 hours, stock solutions of test compounds/plant extracts were made in appropriate solvents (e.g., DMSO). Cells were treated with test material or respective vehicle control diluted in growth medium for 48 hours in a humidified 37° C. incubator with 10% $CO_2$. After incubation, growth medium from each plate was removed and 800 ul of TRIzol Reagent (Invitrogen) was added to the plates. Cell lysates were collected and placed in −80° C. freezer until RNA isolation and analysis.

RNA Isolation

RNA was isolated by following the manufacturer's procedures. Briefly, the cell lysates were brought to room temperature. 0.2 ml of chloroform per 1 ml of TRIzol® Reagent was added. The tubes were shaken vigorously for 15 seconds and incubated at ambient temperature for 2 to 3 minutes. The samples were centrifuged at 12,000×g for 15 minutes at 2 to 8° C. Following centrifugation; the mixture separated into multiple phases, and RNA remains exclusively in the upper aqueous phase.

The aqueous phase was then transferred to a fresh tube. The RNA was precipitated from the aqueous phase by mixing with 0.5 ml of isopropyl alcohol per 1 ml of TRIzol® Reagent was used for the initial homogenization. Samples were incubated at 15 to 30° C. for 10 minutes and centrifuged at 12,000×g for 10 minutes at 2 to 8° C. The supernatant was removed, and the RNA pellet was washed once with 75% ethanol by adding at least 1 ml of 75% ethanol per 1 ml of TRIzol® Reagent used for the cell lysate. The sample was mixed by vortexing and centrifuged at 7,500×g for 5 minutes at 2 to 8° C. The RNA pellet was briefly air dried. RNA was dissolved in RNase-free water, and the concentration of total RNA was determined by using Nanodrop (Thermo Scientific, DE).

Reverse Transcriptase and qPCR

Reverse Transcription (RT) reactions were conducted in a total volume of 20 μl. The RT mixture was prepared to contain 2 μl 10× TaqMan RT buffer, 4.4 μl 25 mM MgCl2, 4.0 μl dNTP mix, 1.0 μl Random Hexamer, 0.4 μl RNase Inhibitor, 0.5 μl MultiScribe Reverse Transcriptase (50 U/ml), 2.0 μg of RNA, and RNase-free water to make up the final volume of 20 μl. The reaction was incubated at 25° C. for 10 min, 48° C. for 30 min, then 95° C. for 5 min using Stratagene Mx 3005P QPCR machine. After the RT step, the reactions were stored at −20° C. for qPCR analysis.

Quantitative Polymerase Chain Reaction (qPCR) was conducted in a total volume of 20 μl. Applied Biosystems (AB) Universal PCR master mix was used. The mixture was prepared to contain 10 μl of Taqman Universal PCR mix, 1 μl of primer and probe mix, 2 μl of RT product, and 7 μl of deionized water. Both MAGP-1 and GAPDH primers and probes were purchased from Applied Biosystems, and ID for MAGP-1 is Hs00250064_ml, and Part number for human GAPDH is 4352934E.

The temperature profiles for QPCR were 50° C. for 2 min, and 95° C. for 10 min for 1 cycle, then at 95° C. for 15 sec, and 60° C. for 1 min for 40 cycles. Values for MAGP-1 mRNA were collected along with those for the reference genes GAPDH. Values are normalized to GAPDH to determine changes in MAGP-1 mRNA after treatment. Percent increase in mRNA for MAGP-1 was calculated by comparing the test results to the vehicle control.

Table 1 lists ingredients that were determined to be active at stimulating expression of MAGP-1.

TABLE 1

MAGP-1 Screening Data

| Product/Ingredient Name | Concentration | Activity Level (see Key) |
|---|---|---|
| KTFK | 0.001% | ++++ |
| Amorphophallus campanulatus | 0.1% | ++++ |
| Sesbania grandiflora | 0.01% | + |
| Thiodipropionic acid (TDPA) | 0.001% | ++ |
| Sapindus rarak | 0.001% | ++ |
| Compound of structure I | 0.01% | ++++ |
| Antidesma bunius | 0.10% | +++ |
| Tiliacora triandra | 0.01% | +++ |
| Compound of structure II | 0.01% | ++++ |
| Thunbergia laurifolia | 0.01% | + |
| Operculina turpethum | 0.00% | ++ |
| Ixora chinensis | 0.01% | +++ |
| Clerodendron lindleyi | 0.001% | + |

Key to activity
0: 0-20%
+: 21-40%
++: 41-60%
+++: 61-80%
++++: >80%

All percentages are by weight, based on the total weight of the composition, unless otherwise indicated.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for improving the condition or aesthetic appearance of human skin comprising topically applying to skin in need thereof an effective amount of a composition comprising:
   (i) a MAGP-1 active agent is
      an ethanolic extract of *Antidesma bunius*, and
   (ii) a cosmetically acceptable vehicle,
wherein said improvement is selected from the group consisting of:
   (a) treatment, reduction, and/or prevention of fine lines or wrinkles,
   (b) reduction of skin pore size,
   (c) improvement in skin thickness, plumpness, and/or firmness;
   (d) improvement in skin suppleness and/or softness;
   (e) improvement in skin tone, radiance, and/or clarity;
   (f) improvement in procollagen and/or collagen production;
   (g) improvement in maintenance and remodeling of elastin;
   (h) improvement in skin texture and/or promotion of retexturization;
   (i) improvement in skin barrier repair and/or function;
   (j) improvement in appearance of skin contours;
   (k) restoration of skin luster and/or brightness;
   (l) replenishment of essential nutrients and/or constituents in the skin;
   (m) improvement of skin appearance decreased by menopause;
   (n) improvement in skin moisturization;
   (o) increase in skin elasticity and/or resiliency;
   (p) treatment, reduction, and/or prevention of skin sagging; and
   (q) reduction of pigment spots; or any combination thereof.

2. The method according to claim 1, wherein said improvement is the treatment, reduction, and/or prevention of fine lines or wrinkles.

3. The method according to claim 1, wherein said improvement is an increase in skin elasticity and/or resiliency.

4. The method according to claim 1, wherein said improvement is the treatment, reduction, and/or prevention of skin sagging.

5. The method according to claim 1, wherein the composition is topically applied at least once daily for at least one week.

* * * * *